(12) United States Patent
Wang et al.

(10) Patent No.: US 12,082,874 B2
(45) Date of Patent: *Sep. 10, 2024

(54) IRRIGATED ABLATION ELECTRODE ASSEMBLY HAVING OFF-CENTER IRRIGATION PASSAGEWAY

(71) Applicant: St Jude Medical, Atrial Fibrillation Division, Inc, St. Paul, MN (US)

(72) Inventors: Huisun Wang, Maple Grove, MN (US); Christopher J. Geurkink, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 932 days.

This patent is subject to a terminal disclaimer.

(21) Appl. No.: 16/848,599

(22) Filed: Apr. 14, 2020

(65) Prior Publication Data

US 2020/0305971 A1    Oct. 1, 2020

Related U.S. Application Data

(63) Continuation of application No. 16/134,503, filed on Sep. 18, 2018, now Pat. No. 10,653,481, which is a
(Continued)

(51) Int. Cl.
*A61B 18/14*    (2006.01)
*A61M 25/00*    (2006.01)
(Continued)

(52) U.S. Cl.
CPC ..... *A61B 18/1492* (2013.01); *A61M 25/0069* (2013.01); *A61M 25/007* (2013.01);
(Continued)

(58) Field of Classification Search
CPC ............ A61M 25/0069; A61M 25/007; A61B 2218/002; A61B 2018/002;
(Continued)

(56) References Cited

U.S. PATENT DOCUMENTS

5,971,968 A * 10/1999 Tu ........................ A61M 25/007
 604/264
6,210,406 B1 * 4/2001 Webster ............. A61B 18/1492
 606/41
(Continued)

*Primary Examiner* — Chelsea E Stinson
*Assistant Examiner* — Anh Bui
(74) *Attorney, Agent, or Firm* — Armstrong Teasdale LLP (57) ABSTRACT

An irrigated ablation catheter includes a shaft and an electrode assembly affixed to a distal end of the shaft. The distal electrode assembly includes a manifold and an ablation electrode affixed together and extending along a center axis. The electrode has a distal irrigation passageway extending therethrough to an opening at a distal tip of the electrode. The opening of the irrigation passageway is offset in distance from the center axis, and allows a thermal sensor such as a thermocouple to be located in a sensor cavity in the electrode on or near the center axis. One variation involves providing a pair of distal irrigation passageways through the electrode where both of the openings of the passageways are offset from the center axis. The thermal sensor in this variation is located in the sensor cavity substantially on the center axis.

20 Claims, 6 Drawing Sheets

Related U.S. Application Data continuation of application No. 12/347,270, filed on Dec. 31, 2008, now Pat. No. 10,105,177.

(51) Int. Cl.
*A61B 17/00* (2006.01)
*A61B 18/00* (2006.01)

(52) U.S. Cl.
CPC ............ *A61B 2017/00084* (2013.01); *A61B 2017/00088* (2013.01); *A61B 2017/00092* (2013.01); *A61B 2018/00011* (2013.01); *A61B 2018/00029* (2013.01); *A61B 2018/00577* (2013.01); *A61B 2018/00702* (2013.01); *A61B 2018/00791* (2013.01); *A61B 2018/00797* (2013.01); *A61B 2018/00809* (2013.01); *A61B 2018/00815* (2013.01); *A61B 2018/00821* (2013.01); *A61B 2218/002* (2013.01); *Y10T 29/49826* (2015.01)

(58) Field of Classification Search
CPC ........... A61B 2018/00791; A61B 2018/00797; A61B 2018/00809; A61B 2018/00815; A61B 2018/00821; A61B 2018/00011; A61B 2018/00029; A61B 2018/00577; A61B 2017/0084; A61B 2017/00088; A61B 2017/00092
See application file for complete search history.

(56) References Cited

U.S. PATENT DOCUMENTS

| | | | |
|---|---|---|---|
| 7,263,397 | B2 | 8/2007 | Hauck et al. |
| 7,815,635 | B2 | 10/2010 | Wittkampf et al. |
| 10,105,177 | B2 * | 10/2018 | Wang ................ A61M 25/007 |
| 10,653,481 | B2 * | 5/2020 | Wang ................ A61M 25/007 |
| 2004/0054272 | A1 | 3/2004 | Messing |
| 2004/0267106 | A1 | 12/2004 | Segner et al. |
| 2006/0184165 | A1 | 8/2006 | Webster et al. |
| 2007/0270791 | A1 * | 11/2007 | Wang ................ A61B 18/148 606/41 |
| 2008/0045943 | A1 | 2/2008 | Wittkampf et al. |
| 2008/0091193 | A1 | 4/2008 | Kauphusman et al. |
| 2008/0249522 | A1 * | 10/2008 | Pappone ............... A61B 18/18 606/41 |
| 2009/0259222 | A1 | 10/2009 | Wang et al. |

\* cited by examiner

IRRIGATED ABLATION ELECTRODE ASSEMBLY HAVING OFF-CENTER IRRIGATION PASSAGEWAY

CROSS-REFERENCE TO RELATED APPLICATIONS

This application is a continuation of U.S. application Ser. No. 16/134,503, filed 18 Sep. 2018 (the '503 application), which is a continuation of U.S. application Ser. No. 12/347,270, filed 31 Dec. 2008 (the '270 application) now U.S. Pat. No. 10,105,177. The '503 application and the '270 application are both hereby incorporated by reference as though fully set forth herein.

BACKGROUND OF THE INVENTION a. Field of the Invention

The present invention relates generally to irrigated ablation catheters, and more particularly, to electrode assemblies having one or more distal irrigation passageways that are off-center.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature and to the intended site, for example, a site within the patient's heart, and carries one or more electrodes, which may be used for mapping, ablation, diagnosis, or other treatments.

There are a number of methods used for ablation of desired areas, including, for example, radio frequency (RF) ablation. RF ablation is accomplished by transmission of radio frequency energy to a desired target area through an electrode assembly to ablate tissue at the target site. Because RF ablation may generate significant heat, which if not controlled can result in undesired or excessive tissue damage, such as steam pop, tissue charring, and the like, it is commonly desirable to include a mechanism to irrigate the target area and the device with biocompatible fluids, such as a saline solution. The use of irrigated ablation catheters can also prevent the formation of soft thrombus and/or blood coagulation.

Typically, there are two general classes of irrigated electrode catheters, i.e., open irrigation catheters and closed irrigation catheters. Closed ablation catheters usually circulate a cooling fluid within the inner cavity of the electrode. Open ablation catheters typically deliver the cooling fluid through open outlets or openings on or about an outer surface of the electrode. Open ablation catheters often use the inner cavity of the electrode, or distal member, as a manifold to distribute saline solution, or other irrigation fluids, to one or more passageways that lead to openings/outlets provided on the surface of the electrode. The saline thus flows directly through the outlets of the passageways onto or about the distal electrode member. This direct flow of fluid through the electrode tip lowers the temperature of the tip during operation, rendering accurate monitoring and control of the ablative process more difficult.

Another known mechanism to control heat is to provide an ablation generator with certain feedback features, such as a temperature readout of the electrode temperature. To provide for such feedback to the physician/clinician during the procedure, conventional RF ablation generators are typically configured for connection to a temperature sensor, such as a thermocouple, located within the electrode.

A common conventional irrigated ablation catheter design involves the use of a distal irrigation passageway in combination with an electrode-disposed thermal sensor. The distal irrigation passageway is thermally insulated and is typically located on the center axis of the electrode assembly. Because the distal irrigation passageway is located on the center axis, the thermal sensor must be moved away from the center axial position. This off-center positioning of the thermal sensor is less than ideal since it could affect the temperature measurement. For example, consider the situation where the catheter electrode is in a parallel contact orientation. The temperature reading will depend on which side of the electrode is contacting the tissue, since it is on the contact side of the electrode where the significant heat will be generated. The preferred location for the thermal sensor would be on or near the center axis of the electrode.

There is therefore a need to minimize or eliminate one or more of the problems set forth above.

BRIEF SUMMARY OF THE INVENTION

One advantage of the present invention is that is provides an irrigated ablation electrode assembly with an improved and more consistent temperature monitoring capability over a broad range of expected operating orientations. Another advantage of the present invention is that it provides such improved temperature monitoring with no significant impairment to the distal tip irrigation capability.

The present invention is directed to a distal electrode assembly of an irrigated ablation catheter, where the assembly includes a manifold and an ablation electrode, which together extend along a main or center axis. The manifold is configured for connection to a distal end of a shaft portion of the catheter. The ablation electrode has a first irrigation passageway having a first opening at a distal tip thereof. The first opening is offset in distance from the center axis. Moving the distal irrigation passageway vacates space in the center of the electrode, on or near the center axis. Through the foregoing, a thermal or temperature sensor, such as a thermocouple, thermistor or the like, may be disposed within a sensor cavity in the electrode at or near the center axis which overcomes the problems described above.

In one embodiment, the irrigation passageway is thermally insulated, such as through insertion of a thermally insulated tubular element. In another embodiment, the distal assembly includes first and second irrigation passageways with respective first and second openings at the distal tip of the electrode to define a dual distal irrigation passageway ablation electrode assembly. These dual irrigation passageways have respective openings that are both offset in distance from the center axis so as to allow the temperature sensor to be placed at or near the center axis, thereby improving temperature monitoring performance.

A catheter including the inventive electrode assembly and a method of manufacturing an irrigated ablation catheter are also presented.

DETAILED DESCRIPTION OF THE INVENTION

Figure 1:
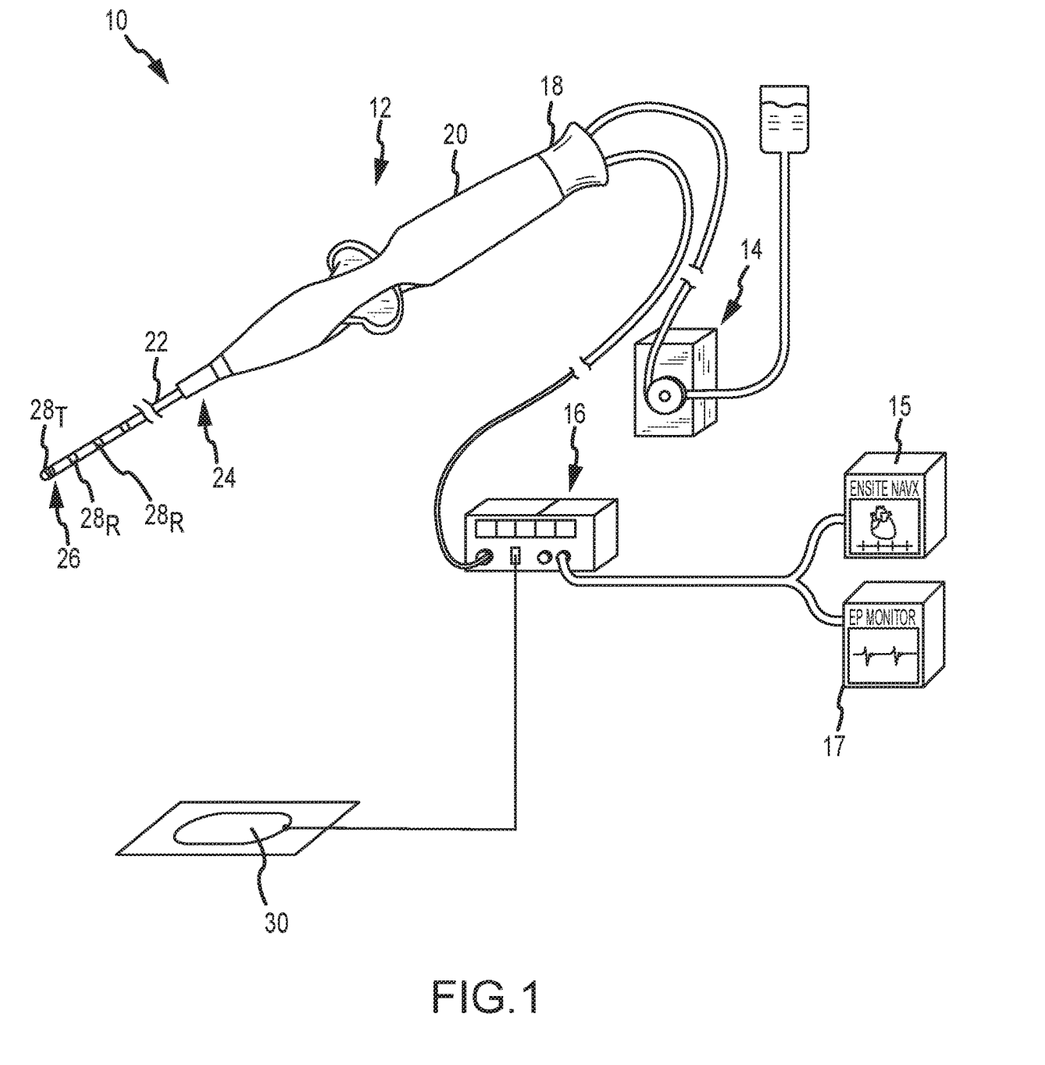
FIG. 1 is a diagrammatic view of an exemplary RF ablation environment in which embodiments of the invention may be used.

Referring now to the drawings wherein like reference numerals are used to identify identical components in the various views, FIG. 1 is a simplified, perspective view of a system 10 for conducting a diagnostic or therapeutic function, which in the illustrated embodiment shows an RF ablation configuration. The system 10 includes an irrigated ablation catheter 12 operably connected to a fluid source 14, such as a pump assembly, and an energy source, such as an RF ablation generator 16. FIG. 1 generally illustrates an irrigated ablation catheter 12 of the type that may be provided by and/or used in connection with the present invention. The remainder of the system 10 may comprise conventional components. In this regard, the fluid source 14 and the RF ablation generator 16 may serve to facilitate the operation of an ablation procedure and may involve monitoring any number of chosen variables (e.g., temperature of the ablation electrode, ablation energy) and providing the requisite energy source. Furthermore, additional components may be integrated into the system 10, such as visualization, mapping and navigation components known in the art, including among others, for example, an EnSite NavX™ system 15 commercially available from St. Jude Medical, Inc., and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. Additionally, an electrophysiological (EP) monitor or display such as an electrogram signal display 17, or other systems conventional in the art may also be integrated into the system 10. It should be understood that embodiments consistent with the present invention may, and typically will, include other features not shown or described herein in FIG. 1 for the sake of brevity and clarity. For example, an irrigated ablation catheter may typically include additional electrodes (and corresponding leads) and other features as known in the art.

The catheter 12 may include a cable connector portion or interface 18, a handle 20 and a shaft 22 having a proximal end 24 and a distal end 26. Disposed on the shaft 22 near the distal end is an ablation tip electrode $28_T$. The system 10 may further include an electrical return which is used in cooperation with the ablation electrode $28_T$, such as a skin patch 30 (i.e., an RF dispersive indifferent electrode/patch).

The shaft 22 may further include one or more other electrodes, configured for intra-cardiac use, such as various ring electrodes $28_R$. It should be re-iterated that the catheter 12 may include still other electrodes, and that in any event, in other embodiments, one or more such other electrodes may be used for any number of diagnostic and/or therapeutic purposes. For instance, such electrodes and therefore such catheters may be used for performing ablation procedures as noted, but also for cardiac mapping, electrophysiological (EP) studies and other like procedures.

The general structural and functional features of catheter systems such as those generally comprising the catheter 12, the fluid source 14 and the RF ablation generator 16 are generally well known to those of skill in the art. For example, the fluid source 14 can comprise various known assembly, including fixed volume rolling pumps, variable volume syringe pumps and other pump assembly known to those skill in the art, including a gravity fed supply as shown. The fluid provided by fluid source 14 may comprise a suitable biocompatible fluid, such as saline. The RF ablation generator 16 may comprise conventional apparatus, such as a commercially available unit sold under the model number IBI-1500T RF Cardiac Ablation Generator, available from Irvine Biomedical, Inc. Of course, the RF ablation generator 16 can also comprise other known energy sources.

Figure 2:
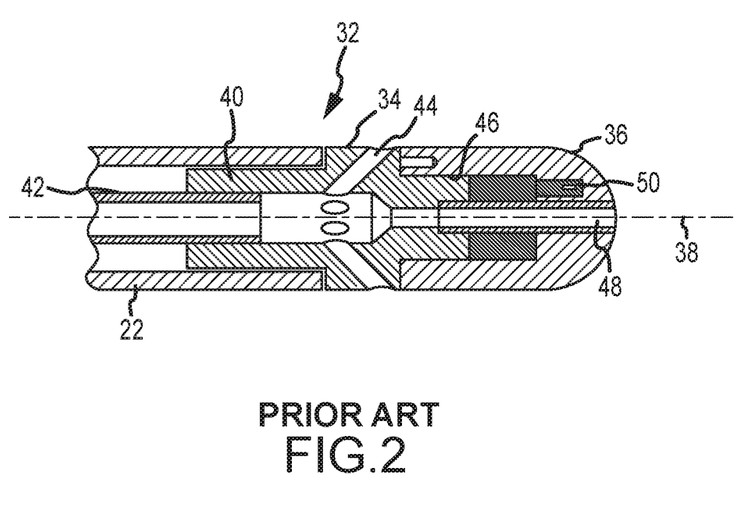
FIG. 2 is a cross-sectional view of an irrigated ablation electrode assembly having a conventional configuration.

FIG. 2 is a cross-sectional view of a conventional distal electrode assembly 32 commonly used in an irrigated ablation electrode design. The assembly 32 includes a manifold 34 and an ablation electrode 36 which extend together along a center (longitudinal) axis 38. The manifold 34 includes a proximal coupling portion 40 that is configured for connection to the shaft 22. The manifold 34 further includes a centrally-disposed distribution cavity that features an inlet and is adapted for connection to an irrigation fluid delivery tube 42. The manifold 34 also includes a plurality of proximal irrigation passageways or ports 44 ("ports") extending from the distribution cavity to the outer surface of the manifold 34. The manifold 34 also includes a distal coupling portion configured in size and shape to mate with a corresponding blind bore 46 formed in the ablation electrode 36. As conventional, a generally straight irrigation passageway 48 is formed through the electrode 36, extending along the center axis 38. Accordingly, a thermal sensor, such as a thermocouple 50 or the like, must be offset significantly from the center axis 38. As described in the Background, this off-center positioning of the sensor can lead to inconsistent temperature measurements, particularly in a parallel contact orientation, depending on which side of the electrode 36 is contacting the tissue (i.e., note, that the sensor 50 is much closer to the "top" side of the electrode and will thus be more sensitive to temperature levels/changes on that side and less sensitive to temperature levels/changes on the other side).

It is desirable to position the thermal sensor on the center axis, at or near the center axial location in the electrode. In order to do so, the distal irrigation passageway, in accordance with the invention, is moved away from its conventional on-axis position to an off-center position. FIGS. 3A-FIG. 6 illustrate various embodiments of the invention; however, common to all the embodiments is the inclusion of (i) one or more distal irrigation passageway(s) with respective openings that are offset in distance from the center axis with (ii) an on-center (or near on-center) located temperature sensor.

Figure 3A:
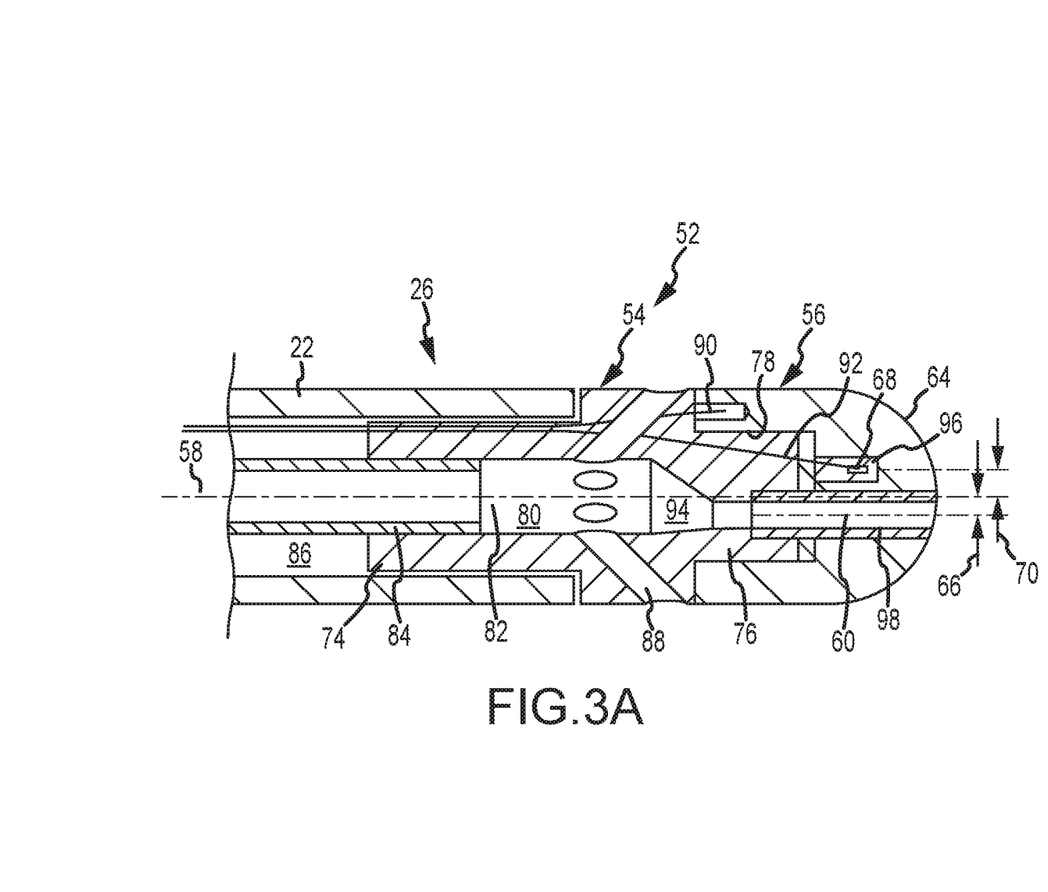
FIG. 3A is a cross-sectional view of a first embodiment of an electrode assembly having a distal irrigation passageway through an ablation electrode, and which has an opening that is offset in distance from a center axis.

FIG. 3A is a cross-sectional view of a first embodiment of a distal electrode assembly 52. The assembly 52 includes a manifold 54 affixed to an ablation electrode 56. Together, the assembly 52 extends along a center (longitudinal) axis 58. The manifold 54 may be generally cylindrical in shape, at least as to its radially-outermost surface. Moreover, many embodiments of electrode 56 are also generally cylindrical in shape, terminating in a hemispherical distal end. The cylindrical shape of the manifold 54 and of the electrode 56 may be substantially similar to one another and generally have the same overall diameter, which can provide or create a flush or substantially smooth outer body or profile for electrode assembly 52. Significantly, as alluded to a defining feature of the assembly 52 is that it includes an off-center distal irrigation passageway 60 with an opening 62 at a distal tip 64 of the electrode 56 where the opening is offset in distance from the center axis. In the first embodiment, the distal irrigation passageway 60 is straight and is substantially parallel to the center axis 58, and whose opening 62 is offset in distance by a first amount 66 from the axis 58. The assembly 52 further includes a thermal or temperature sensor 68, which is illustrated as being located near center, being offset in distance from the center axis 58 by a second amount 70. Note, that the first offset amount 66 need not be greater than the second offset amount 70. It is sufficient that the temperature sensor 68 is closer to the center axis than would otherwise be as per conventional designs using on-axis distal irrigation passageways. Through the foregoing, the temperature sensor 68 can be located closer to the center axis 58 and closer to the axial center of the electrode 56 than that provided for under conventional designs.

Figure 3B:
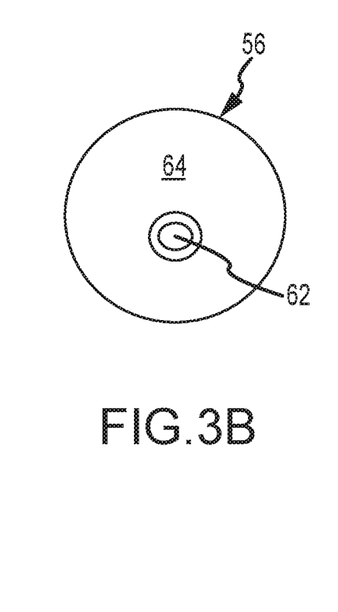
FIG. 3B is a front view of the electrode assembly of FIG. 3A, more clearly showing the distal opening of the off-center irrigation passageway.

FIG. 3B is an axial head-on view showing more clearly the off-center location of the irrigation passageway 60, more particularly the offset in distance of the distal opening 62 from the center axis.

Referring now to FIGS. 3A-3B, the manifold 54 is further configured to provide a plurality of cavities and/or passageways adapted to facilitate the flow of irrigation fluid therethrough to the manifold's outer surface (proximal irrigation) as well as to the electrode 56 for delivery by the distal irrigation passageways (distal irrigation). The manifold 54 is formed of a main body 72, and includes a proximal coupling portion 74 and a distal coupling portion 76. The proximal coupling portion 74 is configured in size and shape to be connected to the distal end 26 of the shaft 22. In the illustrated embodiment, the proximal coupling portion 74 is cylindrical. Likewise, the distal coupling portion 76 is configured in size and shape to be received within a blind bore 78 of the ablation electrode 56 for attachment thereto. The electrode 56 may be connected by various known mechanisms, including adhesives, press-fit configurations, snap-fit configurations, threaded configurations, or various other mechanism known to persons of ordinary skill in the art.

The manifold 54 further includes a centrally-disposed distribution cavity 80, configured for transporting and/or distributing fluid throughout various portions of the electrode assembly 32. The cavity 80 has an inlet 82, which is configured to cooperate with a fluid delivery tube 84. In particular, the fluid delivery tube 84 may be securely provided in fluid communications with the distribution cavity 80 through the insertion of the tube 84 in the inlet 82. An optional seal (not shown) may be provided about (around) the tube 84 after insertion thereof into the inlet 82. The fluid delivery tube 84 may be disposed in a central lumen 86 of the shaft 22, as shown.

The manifold 54 may further include one or more proximal irrigation passageways or ports 88 (hereinafter "ports" 88) extending (e.g., at an acute angle) between the distribution cavity 80 to an outer surface of the manifold 54. The distribution cavity 80 may serve to distribute irrigation fluid to the proximal ports 88. In one embodiment, the manifold 54 may be formed so that a plurality of proximal ports 88 are substantially equally distributed around the circumference of the manifold to provide substantially equal distribution of fluid. It should be understood that the art is replete with various configurations and design approaches for proximal irrigation passageways, and will therefore not be further elaborated upon.

The manifold 54 also includes a tapered lumen portion 94, located intermediate the main, irrigation distribution cavity 80 and the distal irrigation passageway 60, configured to transition the fluid paths from an on-center path (i.e., the cavity 80) to an off-center path (i.e., the distal irrigation passageway 60).

The manifold 54 may also include guideways (not shown) configured to allow one or more electrical connection wires to pass therethrough. For example, a main ablation power wire 90 is shown in FIG. 3A, which is connected at the proximal end to the RF ablation generator 16 (best shown in FIG. 1), is routed through lumen 86 (or other lumen provided within shaft 22), passes through the manifold 54 through such a guideway and is then electrically terminated at the ablation electrode 56. Likewise, a temperature sensor connection wire 92 may also follow a similar path as the power wire 90, and is then electrically terminated at the sensor 68.

The manifold 54 may also comprise thermally nonconductive or reduced (i.e. poor) thermally conductive material that serves to insulate the fluid from the remaining portions of electrode assembly 52, for example, the electrode 56. Moreover, such selected material(s) for the manifold 54 may also exhibit electrically nonconductive properties. Comparatively, the manifold 54 may have lower thermal conductivity than the electrode 56. In one embodiment, the manifold 54 may comprise a reduced thermally conductive polymer material. A reduced thermally conductive material is one with physical attributes that decrease heat transfer by about 10% or more, provided that the remaining structural components are selected with the appropriate characteristics and sensitivities to maintain adequate monitoring and control of the process. Moreover, a reduced thermally conductive material may include polyether ether ketone ("PEEK"). Further examples of reduced thermally conductive materials that may be useful in conjunction with the present invention include, but are not limited to, high-density polytheylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof. Moreover, for some embodiments, the manifold 54 may be substantially less thermally conductive than the electrode 56. As a result, the irrigation fluid flowing through manifold 54 may have very little thermal effect on the electrode 56 due to the poor thermal conductivity of manifold 54 (e.g. less than 5% effect), and preferably may have nearly 0% effect.

The ablation electrode 56 is configured to have an ablation surface, including distal tip 64. The electrode 56 may generally comprise electrically and potentially thermally, conductive materials, as known to those of ordinary skill in the art. Examples of suitable electrically conductive materials include (but are not limited to) gold, platinum, iridium, palladium, stainless steel, and various mixtures, alloys and combinations thereof. In one embodiment, the distal tip 64 may be rounded (e.g., partially spherical or hemispherical), although other configurations may be used.

The electrode 56 is further configured with a sensor cavity 96 that is configured in size and shape to receive the temperature sensor 68. In the illustrated embodiment, the sensor 68 may be disposed near the central longitudinal axis 58. In alternate embodiments described in connection with FIGS. 4A-4B, 5A-5B and 6, the sensor 68 may be located substantially on axis 58. Such improved positioning of the sensor 68 may further enhance the temperature sensing properties or capabilities of the electrode assembly 52. The sensor 68 may comprise conventional components known in the art, including, for example, thermocouples or thermistors. The sensor 68 may further be substantially surrounded, or at least partially encapsulated, by a thermally conductive and electrically non-conductive material. This thermally conductive and electrically non-conductive material can serve to hold temperature sensor 68 in place within the electrode 56 and provide improved heat exchange between the sensor 68 and the electrode 56. Such material may comprise, for example, thermally conductive resins, epoxies, or potting compounds.

The electrode 56 further includes the off-center distal irrigation passageway 60 having the opening 62 that is offset in distance from the center axis, described above. The interior of the passageway 60 may be, and preferably is, thermally insulated from the electrode body, for example, through the use of thermally insulated tubular element 98. This insulation is to minimize temperature disturbances to the sensed electrode temperature that may be introduced by the irrigation fluid lowering the temperature of the electrode body.

Thermally insulated tubular element 98 may comprise thermally non-conductive and/or poor conductive material. Such material may include, but is not limited to, high-density polyethylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof.

Figure 4A:
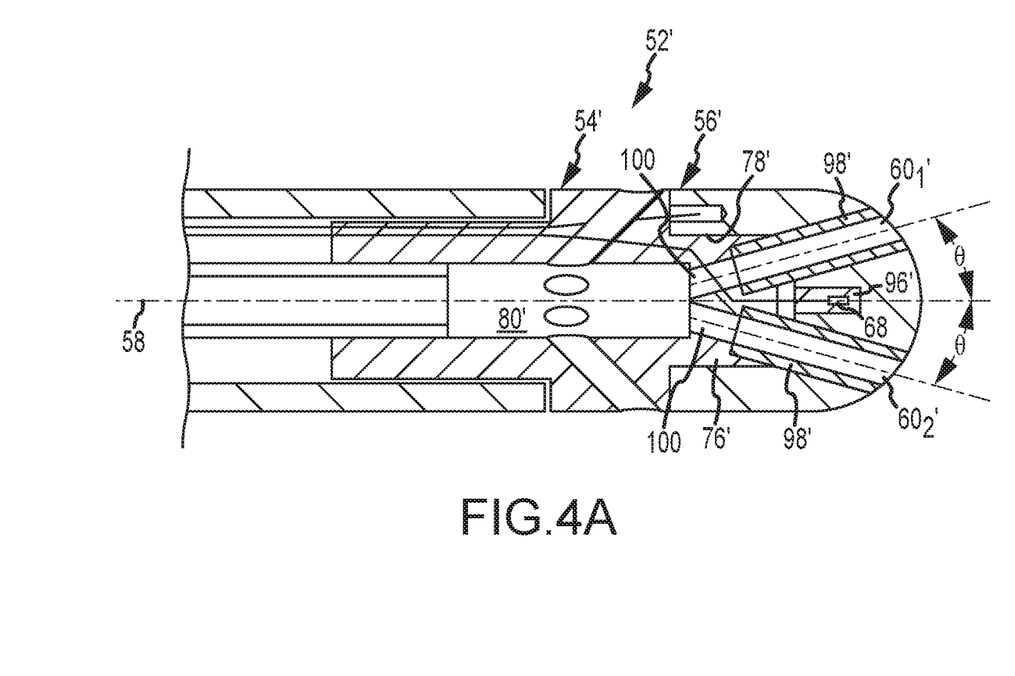
FIG. 4A is a cross-sectional view of a second embodiment of an electrode assembly of the present invention, having dual, straight irrigation passageways having respective openings both of which are offset in distance from the center axis.
Figure 4B:
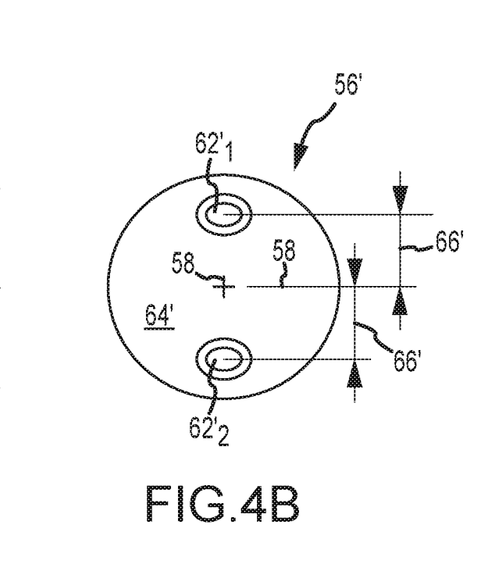
FIG. 4B is a front view of the electrode assembly of FIG. 4A.

FIGS. 4A-4B illustrate a second embodiment of the inventive distal electrode assembly, which is referred to in the drawings as assembly 52'. The assembly 52' is similar to the assembly 52, and thus only the differences will be described. The assembly 52' extends the principle of an off-center irrigation passageway with an opening that is offset in distance from the center axis to a dual passageway embodiment, and which further uses an on-center temperature sensor (in contrast to the near center location for the thermal sensor in the embodiment of FIGS. 3A-3B). The distal irrigation passageways include a first irrigation passageway $60_1'$ and a second irrigation passageway $60_2'$. Each one of the passageways $60_1'$, $60_2'$ are offset from the center axis 58. As shown in FIG. 4A, each passageway $60_1'$, $60_2'$ is generally straight, extending along its own longitudinal axis, which longitudinal axis intersects and forms an acute angle θ with respect to the center axis 58. The acute angle θ may assume a wide range of values, adequate to vacate the space on (or near) the center axis 58 so as to allow the temperature sensor 68 to be mounted therein. In the illustrated embodiment, the angle θ is about 15° (degrees), although it should be appreciated that variations from this angle are possible and still achieve the purpose of vacating the space in and around the center axis 58.

As shown in FIG. 4B, the distal openings of the irrigation passageways $60_1'$, $60_2'$ are also offset in distance from the center axis 58 by a respective offset amount (distance) designated 66'. Although not required, in the illustrated embodiment, both passageways $60_1'$, $60_2'$ (and openings thereof) are offset in the same manner (i.e., the same acute angle θ and the same offset distance 66' from the center axis 58), making the illustrated embodiment symmetrical. Further variations are possible. For example, a three distal irrigation passageway embodiment is contemplated where the three passageways are equally distributed around the distal tip of the ablation electrode (i.e., the first, second and third offset amounts (distances) of the respective openings from the center axis may be the same and the circumferential spacing of the passageways may be the same).

Referring to FIGS. 4A-4B, the assembly 52' includes a manifold 54' and an ablation electrode 56', which are similar to the manifold 54 and electrode 56 described above. Again, only the differences will be described. The manifold 54', rather than having a tapered lumen portion 94, includes a pair of feed lumens 100 formed in the main body that extend away from the distribution cavity 80' towards the passageways at substantially the same angle θ at which the passageways $60_1'$, $60_2'$ are oriented. The passageways $60_1'$, $60_2'$ and the lumens 100 are thus configured such that when the manifold 54' and the electrode 56' are assembled, the passageways are in alignment with a respective one of the lumens 100. This completes a fluid path from the distribution cavity 80' to the distal openings 62' of the passageways $60_1'$, $60_2'$. In addition, the distal coupling portion 76' of the manifold 54' is modified to accommodate the presence of the feed lumens 100, while the receiving bore 78' of the electrode 56' is also modified in a like and complementary way to cooperate with the modified distal coupling portion 76'. Preferably, each passageway $60_1'$, $60_2'$ is thermally insulated, again, such as through the use of thermally insulated tubular elements 98' of a suitable size and length.

The electrode 56' includes a sensor cavity 96' located substantially on the center axis 58, which in turn allows for the temperature sensor 68 to be disposed substantially on the center axis 58 as well, providing improved temperature monitoring as described above.

Figure 5A:
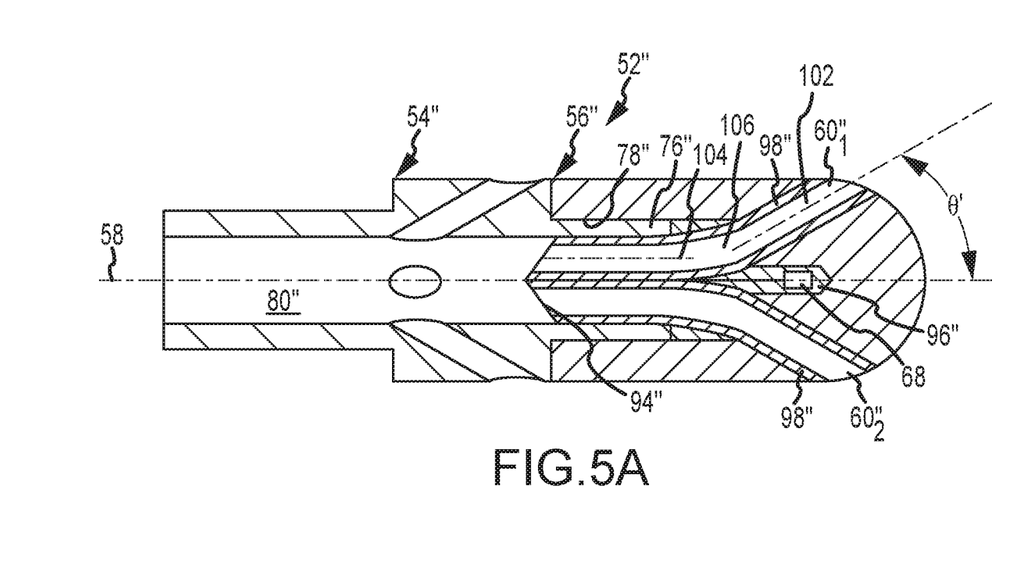
FIG. 5A is a cross-sectional view of a third embodiment of an electrode assembly of the present invention, with dual off-center irrigation passageways having straight and curved sections.
Figure 5B:
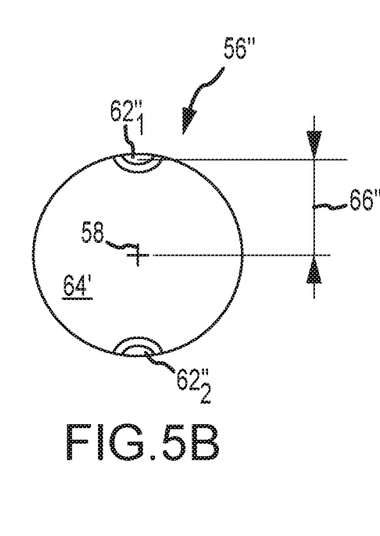
FIG. 5B is a front view of the electrode assembly of FIG. 5A.

FIGS. 5A-5B illustrate a third embodiment of the inventive distal electrode assembly, which is referred to in the drawings as assembly 52". The assembly 52" is similar to assemblies 52 and 52', and thus only the differences will be described. The assembly 52" likewise embodies the principle of off-center distal irrigation passageways having respective openings that are offset in distance from the center axis combined with an on-center temperature sensor. The distal irrigation passageways include a first irrigation passageway $60_1''$ and a second irrigation passageway $60_2''$ having respective distal openings $62_1''$, $62_2''$. (FIG. 5B) that are offset in distance from the center axis. The first and second passageways $60_1''$, $60_2''$ are also offset from the center axis 58. As shown in FIG. 5A, each passageway $60_1''$, $60_2''$ has a respective, generally straight first portion 102, which extends along its own longitudinal axis, which longitudinal axis forms an acute angle θ' with axis 58. Each passageway $60_1''$, $60_2''$ further includes a respective, generally straight second portion 104, which extends along its own longitudinal axis that is generally parallel to the center axis 58. Finally, each passageway $60_1''$, $60_2''$ includes a respective, generally curved portion 106 that is intermediate the first and second straight portions 102, 104. As described, the axis associated with portion 102 intersects with and forms an acute angle θ' with axis 58. The angle θ' may assume a wide range of values selected so that the placement of the passageways vacates the space on (or near) the center axis 58 so as to allow the temperature sensor 68 to be mounted within the electrode 56" on the center axis 58. In the illustrated embodiment, the acute angle θ' is about 30° (degrees), although it should be appreciated that variations from this angle are possible and still achieve the purpose of vacating the space within the electrode 56" on the center axis 58.

As shown in FIG. 5B, the distal openings $62_1"$, $62_2"$ of the irrigation passageways $60_1"$, $60_2"$ are offset in distance from the center axis 58 by an offset amount (distance) designated 66". Although not required, in the illustrated embodiment, both passageways $60_1"$, $60_2"$ and openings thereof $62_1"$, $62_2"$ are offset in the same manner (i.e., the same acute angle θ' and the same offset distance 66" from the center axis 58), making the illustrated embodiment symmetrical.

Referring to FIGS. 5A-5B, the assembly 52" includes a manifold 54" and an ablation electrode 56" that are similar to the manifold 54' and electrode 56' described above. Again, only the differences will be described. The distribution cavity 80" formed in the manifold body extends therethrough on-axis (i.e., similar to a through-bore). The distal coupling portion 76" is modified in view of the change to the distribution cavity 80", while the blind bore 78" of the electrode 56" is also modified in a like and complementary way to cooperate with the modified coupling portion 76". The passageways $60_1"$, $60_2"$ are preferably thermally insulated, such as through the use of thermally insulated tubular elements 98" of a suitable size and length. The distal end of the distribution cavity 80" (i.e., the distal opening of distribution cavity 80") is sized so as to accommodate a pair of such tubular elements 98", in a tight fit relation or in other ways known in the art to effect a secure attachment. The manifold 54" may also include a mechanical feature 94" (e.g., a stop or the like) that impedes any further axial insertion of the tubular elements 98" into the distribution cavity of the manifold once the terminal ends of the tubular elements 98" reach the stop. Once assembled, the tubular elements 98" provide a pair of distal irrigation passageways extending from the distribution cavity 80" to the distal openings on the electrode tip.

The electrode 56" also includes a sensor cavity 96" located substantially on the center axis 58, which in turn allows for the temperature sensor 68 to also be disposed substantially on the center axis 56, providing the improved temperature monitoring as described above.

Figure 6:
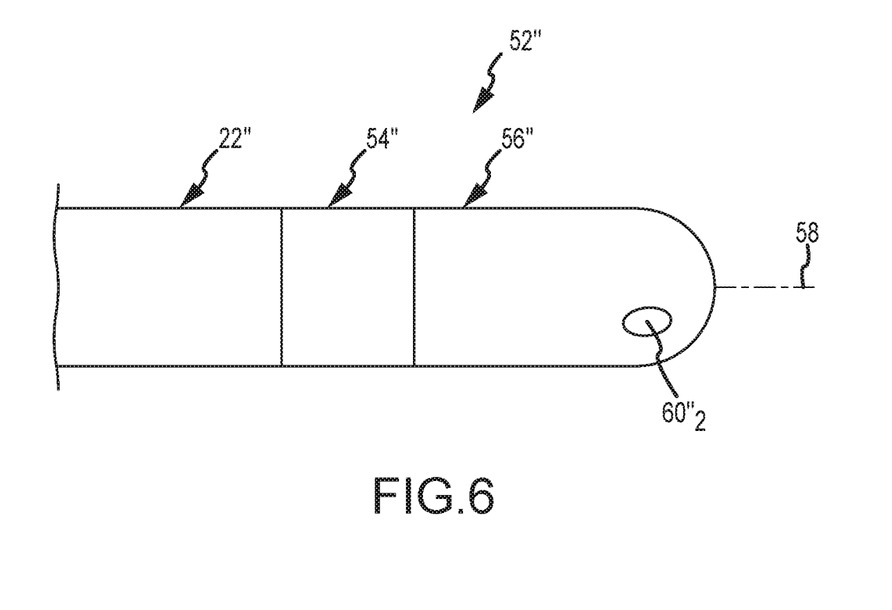
FIG. 6 is a perspective view showing the distal electrode assembly of FIG. 5A.

FIG. 6 is a perspective view of a distal end of a catheter incorporating the inventive electrode assembly 52". As shown, the distal opening $62_2"$ of the irrigation passageway $60_2"$ that is visible in the figure is offset in distance from the center axis 58. As described and illustrated above, the positioning allows for the temperature sensor 68 to be centrally disposed within the electrode 56" on the center axis 58 (or near the center axis in the embodiment of FIGS. 3A-3B).

A method of manufacturing an electrode assembly, in any of the embodiments as described above, is provided and involves a number of steps. First, providing an electrode portion of a distal electrode assembly with a first irrigation passageway having a first opening at a distal tip surface thereof, where the first opening is offset in distance from the center axis of the electrode assembly. The step of providing the electrode may further include the substep of providing a temperature sensor on or near the center axis of the electrode assembly, in the space vacated by moving the irrigation passageway(s) to off-center locations. The next step involves coupling the electrode to a manifold portion of the electrode assembly. Finally, the last step involves coupling the free end of the manifold (i.e. proximal coupling portion of the manifold) to a catheter shaft.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A distal assembly of an irrigated ablation catheter, comprising:
   a manifold extending along a central axis;
   an electrode coupled to a distal end of the manifold;
   the manifold comprising a distribution cavity, wherein the manifold is configured for connection to a distal end of a shaft of the catheter, wherein a longitudinal axis of a distal end portion of the distribution cavity is offset in distance from the central axis by a first amount of offset, and wherein the distal end portion of the distribution cavity extends through the electrode along a direction parallel to the central axis; and
   the electrode comprising a first irrigation outlet, the first irrigation outlet offset in distance from the central axis by the first amount of offset, wherein the first irrigation outlet of the electrode aligns with the distal end portion of the distribution cavity.

2. The assembly of claim 1 further comprising a thermal sensor, wherein the thermal sensor and the electrode are configured to be thermally insulated from an irrigant.

3. The assembly of claim 2, wherein the thermal sensor comprises one of a thermocouple or a thermistor.

4. The assembly of claim 1 wherein the first irrigation outlet comprises a first opening at a distal tip of the electrode.

5. The assembly of claim 1 wherein the manifold comprises a main body having the distribution cavity in communication with an inlet for connection to a supply of irrigation fluid, the manifold further including one or more proximal irrigation ports extending from the distribution cavity to an outer surface of the manifold, the distribution cavity and the one or more proximal irrigation ports being arranged for fluid communication therebetween.

6. The assembly of claim 5 wherein the distribution cavity comprises a tapered lumen portion.

7. The assembly of claim 1 wherein the electrode further comprises a second irrigation outlet having a second opening on a distal tip of the electrode.

8. The assembly of claim 7 wherein the first and second outlets are substantially symmetrical with respect to the central axis.

9. The assembly of claim 8 wherein the electrode further includes a third irrigation outlet having a third opening on the distal tip of the electrode.

10. The assembly of claim 7 wherein the manifold includes a main body having a proximal coupling portion configured for connection to the catheter shaft and a distal coupling portion configured for connection to the electrode, the manifold having the distribution cavity in communication with an inlet for connection to a supply of irrigation fluid, the manifold further including a pair of feed lumens extending from the distribution cavity and configured for respective alignment with first and second irrigation passageways.

11. The assembly of claim 10 wherein the manifold includes a main body having a proximal coupling portion configured for connection to the catheter shaft and a distal coupling portion configured for connection to the electrode, the manifold having distribution cavity in communication with an inlet for connection to a supply of irrigation fluid, the distribution cavity comprising a distal opening configured in size and shape to receive a pair of thermally insulated tubular elements associated with the first and second irrigation passageways.

12. The assembly of claim 1 wherein the electrode comprises a first irrigation passageway comprising a lumen axis and wherein the lumen axis is offset in distance from the central axis by a second amount of offset.

13. The assembly of claim 1 further comprising a thermal sensor, and wherein the manifold further comprises a reduced thermally conductive material configured to insulate the thermal sensor and the electrode from the distribution cavity.

14. An irrigated ablation catheter, comprising
   a shaft having a proximal end and a distal end;
   a manifold comprising a distribution cavity, wherein the manifold is configured for connection to the distal end of the catheter shaft, and wherein a longitudinal axis of a distal end portion of the distribution cavity is offset in distance from a central axis of the manifold by a first amount of offset; and
   an electrode coupled to a distal end of the manifold, the electrode including a first irrigation outlet, the first irrigation outlet offset in distance from the central axis by the first amount of offset, wherein the first irrigation outlet of the electrode aligns with the distal end portion of the distribution cavity, and wherein the distal end portion of the distribution cavity extends through the electrode along a direction parallel to the central axis.

15. The catheter of claim 14 further comprising a thermal sensor, wherein the thermal sensor and the electrode are configured to be thermally insulated from the distribution cavity.

16. The catheter of claim 14 wherein the electrode further includes a second irrigation outlet having a second opening on a distal tip of the electrode, the second irrigation outlet being offset in distance from the central axis by a second amount of offset.

17. The catheter of claim 14 wherein the first irrigation outlet comprises a lumen axis and wherein the lumen axis is offset in distance from the central axis by a second amount of offset.

18. The catheter of claim 14 wherein the first irrigation outlet comprises a first opening at a distal tip of the electrode.

19. The catheter of claim 14 wherein the manifold further comprises a reduced thermally conductive material, and wherein the reduced thermally conductive material is configured to insulate a temperature sensor and the electrode from the irrigant.

20. A method of manufacturing an irrigated ablation catheter including an electrode assembly extending along a center axis, the method comprising
   providing an electrode of the electrode assembly with an irrigation outlet having a distal opening at a distal tip of the electrode, wherein the distal opening is offset in distance from the center axis;
   coupling the electrode to a manifold to form the assembly, wherein the manifold comprises a distribution cavity, wherein a longitudinal axis of a distal end portion of the distribution cavity is offset in distance from the central axis by a first amount of offset, wherein the distal end portion of the distribution cavity extends through the electrode along a direction parallel to the central axis, and wherein the irrigation outlet of the electrode portion aligns with the distal end portion of the distribution cavity; and
   coupling the assembly to a catheter shaft.

* * * * *